United States Patent
Higuchi et al.

(10) Patent No.: US 10,918,456 B2
(45) Date of Patent: Feb. 16, 2021

(54) PROTECTIVE COVER AND MEDICAL OBSERVATION APPARATUS

(71) Applicant: Sony Olympus Medical Solutions Inc., Tokyo (JP)

(72) Inventors: Gakuji Higuchi, Tokyo (JP); Yasuhiro Okabe, Kanagawa (JP); Hidenori Taguchi, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 358 days.

(21) Appl. No.: 15/887,192

(22) Filed: Feb. 2, 2018

(65) Prior Publication Data
US 2018/0221106 A1    Aug. 9, 2018

(30) Foreign Application Priority Data

Feb. 3, 2017 (JP) .............................. JP2017-018180
Dec. 7, 2017 (JP) .............................. JP2017-235532

(51) Int. Cl.
| | |
|---|---|
| A61B 90/00 | (2016.01) |
| A61B 90/50 | (2016.01) |
| A61B 46/10 | (2016.01) |
| A61B 1/00 | (2006.01) |
| A61B 50/00 | (2016.01) |
| A61B 90/25 | (2016.01) |
| A61B 17/00 | (2006.01) |

(52) U.S. Cl.
CPC ............ *A61B 90/361* (2016.02); *A61B 46/10* (2016.02); *A61B 50/00* (2016.02); *A61B 90/50* (2016.02); *A61B 1/00147* (2013.01); *A61B 90/25* (2016.02); *A61B 2017/00477* (2013.01); *A61B 2090/3612* (2016.02); *A61B 2090/371* (2016.02); *A61B 2090/508* (2016.02)

(58) Field of Classification Search
CPC ................ A61B 2562/18; A61B 6/102; A61B 2050/005; A61B 90/20; A61B 90/25; A61B 1/00149; A61B 2017/00336; A61B 1/00–32; A61B 34/30–37; A61B 50/00–39
See application file for complete search history.

(56) References Cited

U.S. PATENT DOCUMENTS

| | | | | |
|---|---|---|---|---|
| 4,157,709 A | * | 6/1979 | Schuster ............ | A61B 10/0291 600/572 |
| 5,105,455 A | * | 4/1992 | Kato ...................... | A61B 6/102 250/227.16 |
| 5,413,556 A | * | 5/1995 | Whittingham ...... | A61F 9/00745 604/22 |
| 5,445,641 A | * | 8/1995 | Frigg ................. | A61B 17/1735 221/113 |

(Continued)

FOREIGN PATENT DOCUMENTS

JP      2005-204898       8/2005

*Primary Examiner* — Timothy J Neal
*Assistant Examiner* — Jae Woo
(74) *Attorney, Agent, or Firm* — Xsensus LLP

(57) ABSTRACT

There is provided a protective cover including: an installation section configured to be installed on an arm that supports an imaging device, the arm including a plurality of links joined to each other by one or a plurality of joint sections; and a protective section configured to cover the imaging device.

17 Claims, 10 Drawing Sheets

(56) References Cited

U.S. PATENT DOCUMENTS

| | | | | |
|---|---|---|---|---|
| 5,944,179 A * | 8/1999 | Walker | | B65D 59/06 |
| | | | | 206/305 |
| 2002/0103419 A1 * | 8/2002 | Christopher | | A61B 1/00073 |
| | | | | 600/156 |
| 2002/0161282 A1 * | 10/2002 | Fulghum | | A61B 1/00009 |
| | | | | 600/160 |
| 2003/0008083 A1 * | 1/2003 | Harhen | | B29C 51/08 |
| | | | | 428/34.1 |
| 2003/0083552 A1 * | 5/2003 | Remijan | | A61B 1/00135 |
| | | | | 600/182 |
| 2003/0236517 A1 * | 12/2003 | Appling | | A61B 18/24 |
| | | | | 606/7 |
| 2004/0006344 A1 * | 1/2004 | Nguyen | | A61B 17/3431 |
| | | | | 606/191 |
| 2005/0067308 A1 * | 3/2005 | Thompson | | A61B 17/34 |
| | | | | 206/363 |
| 2005/0149072 A1 * | 7/2005 | DeVries | | A61B 1/32 |
| | | | | 606/153 |
| 2005/0182298 A1 * | 8/2005 | Ikeda | | A61B 1/00149 |
| | | | | 600/146 |
| 2005/0234493 A1 * | 10/2005 | Carr | | A61B 17/7098 |
| | | | | 606/181 |
| 2006/0021891 A1 * | 2/2006 | Franer | | A61B 17/34 |
| | | | | 206/363 |
| 2006/0079884 A1 * | 4/2006 | Manzo | | A61B 34/30 |
| | | | | 606/41 |
| 2006/0094932 A1 * | 5/2006 | Goldfarb | | A61B 17/02 |
| | | | | 600/229 |
| 2006/0161138 A1 * | 7/2006 | Orban, III | | A61B 34/35 |
| | | | | 606/1 |
| 2006/0178556 A1 * | 8/2006 | Hasser | | A61B 1/00149 |
| | | | | 600/102 |
| 2007/0016226 A1 * | 1/2007 | Campbell | | A61M 37/0069 |
| | | | | 606/116 |
| 2007/0038216 A1 * | 2/2007 | Hamada | | A61B 17/02 |
| | | | | 606/53 |
| 2007/0043338 A1 * | 2/2007 | Moll | | A61B 34/71 |
| | | | | 606/1 |
| 2007/0087602 A1 * | 4/2007 | Smith | | A61L 2/26 |
| | | | | 439/164 |
| 2007/0093792 A1 * | 4/2007 | Julian | | A61B 34/76 |
| | | | | 606/1 |
| 2007/0151390 A1 * | 7/2007 | Blumenkranz | | B25J 15/0009 |
| | | | | 74/490.06 |
| 2007/0255211 A1 * | 11/2007 | Young | | A61B 50/362 |
| | | | | 604/110 |
| 2007/0299427 A1 * | 12/2007 | Yeung | | B25J 9/047 |
| | | | | 606/1 |
| 2009/0086495 A1 * | 4/2009 | Chen | | A61B 90/35 |
| | | | | 362/427 |
| 2009/0275833 A1 * | 11/2009 | Ikeda | | A61B 8/0833 |
| | | | | 600/443 |
| 2011/0028790 A1 * | 2/2011 | Farr | | A61B 1/00045 |
| | | | | 600/187 |
| 2011/0266124 A1 * | 11/2011 | Culp | | A61B 17/32002 |
| | | | | 200/335 |
| 2012/0010611 A1 * | 1/2012 | Krom | | A61B 18/1445 |
| | | | | 606/41 |
| 2012/0035605 A1 * | 2/2012 | Tegg | | A61B 18/1492 |
| | | | | 606/41 |
| 2012/0241497 A1 * | 9/2012 | Mandakolathur Vasudevan | | A61B 17/00491 |
| | | | | 227/176.1 |
| 2013/0199947 A1 * | 8/2013 | Tennican | | A61F 15/004 |
| | | | | 206/216 |
| 2014/0235943 A1 * | 8/2014 | Paris | | A61B 1/015 |
| | | | | 600/109 |
| 2015/0100066 A1 * | 4/2015 | Kostrzewski | | A61B 34/30 |
| | | | | 606/130 |
| 2015/0112141 A1 * | 4/2015 | Oginski | | A61B 1/00131 |
| | | | | 600/136 |
| 2015/0182205 A1 * | 7/2015 | Millard | | A61B 10/04 |
| | | | | 600/424 |
| 2015/0250550 A1 * | 9/2015 | Dawson | | A61B 50/39 |
| | | | | 134/42 |
| 2015/0313679 A1 * | 11/2015 | Fukushima | | G05B 15/02 |
| | | | | 600/102 |
| 2016/0331476 A1 * | 11/2016 | Yoon | | A61B 46/27 |
| 2017/0052358 A1 * | 2/2017 | Higuchi | | H04N 7/185 |
| 2017/0119240 A1 * | 5/2017 | Millard | | A61B 1/05 |
| 2018/0081160 A1 * | 3/2018 | Hirose | | G02B 21/24 |
| 2018/0370045 A1 * | 12/2018 | Kan | | A61B 34/71 |
| 2019/0083182 A1 * | 3/2019 | Roach | | B25J 19/0083 |
| 2019/0314107 A1 * | 10/2019 | Worrell | | A61B 34/70 |

* cited by examiner

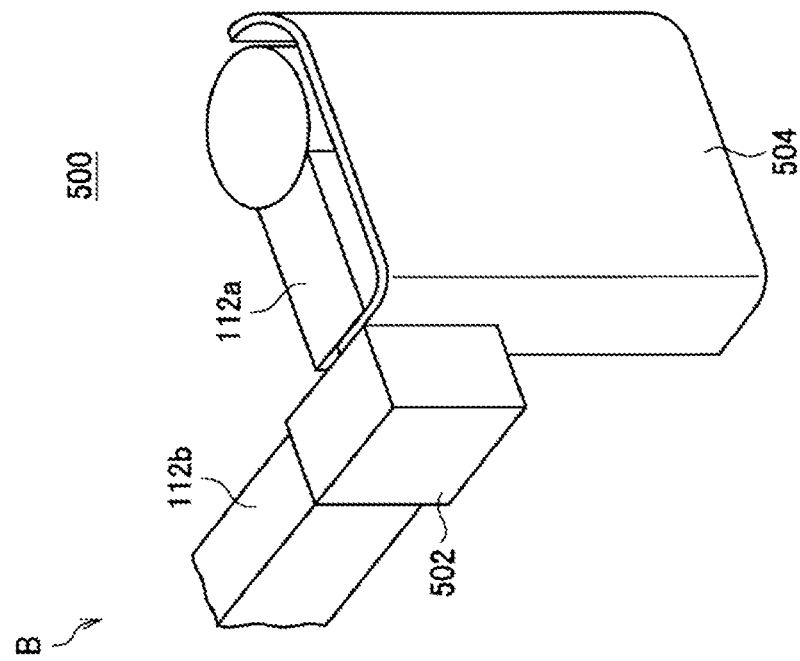
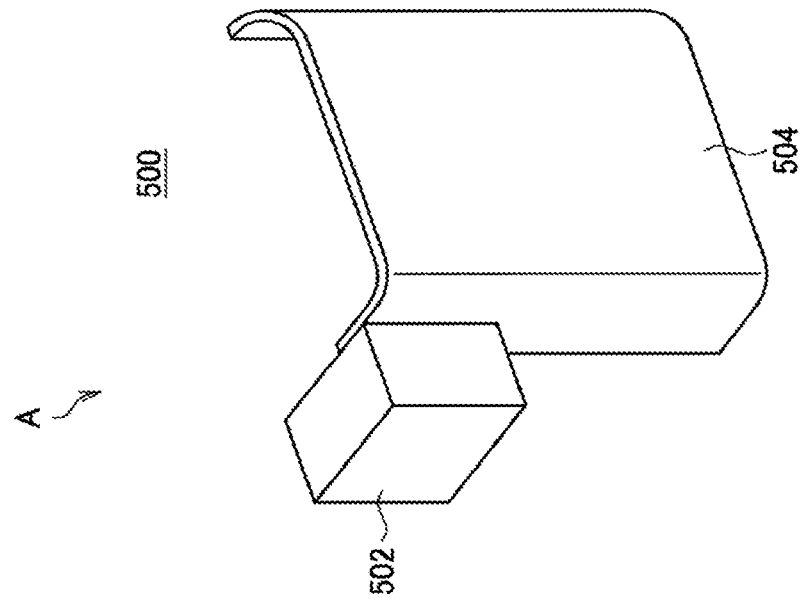
FIG. 10

PROTECTIVE COVER AND MEDICAL OBSERVATION APPARATUS

CROSS REFERENCE TO RELATED APPLICATIONS

This application claims the benefit of Japanese Priority Patent Application JP 2017-018180 filed Feb. 3, 2017, and Japanese Priority Patent Application JP 2017-235532 filed Dec. 7, 2017, the entire contents of each of which are incorporated herein by reference.

BACKGROUND

The present disclosure relates to a protective cover and a medical observation apparatus.

Recently, in the medical field, to support surgeries, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases.

With an electronic imaging medical observation apparatus, along with the increased image quality of imaging devices, the increased image quality of display devices on which taken images are displayed, and the like, the same or higher image quality than an optical medical observation apparatus has come to be obtained. Also, because a user who uses an electronic imaging medical observation apparatus (for example, medical personnel such as a surgeon or a surgeon's assistant) is not required to peer into an eyepiece lens included in an optical microscope like in the case of using an optical medical observation apparatus, it is possible to move the position of the imaging device more freely. For this reason, using an electronic imaging medical observation apparatus has an advantage of enabling more flexible support of surgery by the movement of the position of the imaging device, and in the medical field, utilization of electronic imaging medical observation apparatus is progressing.

Among these, technologies related to the protection of the imaging device provided in the electronic imaging medical observation apparatus are being developed. Examples of the above technologies include the technology described in JP 2005-204898A.

SUMMARY

The imaging device provided in the medical observation apparatus includes a precise mechanism for improving the observation performance, and moreover, fine optical adjustments are performed in the imaging device. For this reason, for example, if the imaging device collides with a wall or the like when the medical observation apparatus is moved, the mechanism included in the imaging device may suffer damage due to the shock of colliding with the wall or the like, and an undesirable situation may occur, such as the imaging device ceasing to function normally, or the optical adjustments becoming misaligned and the observation performance becoming degraded. Also, in a case in which an undesirable situation like the above occurs, repair or replacement of the medical observation apparatus may become necessary, which is very costly.

Herein, in the technology described in JP 2005-204898A, for example, a protective cover that protects the imaging devices is disposed on a support mechanism that supports the imaging device. Thus, by using the technology described in JP 2005-204898A, for example, protecting the imaging device with the protective cover becomes possible, and there is a possibility of being able to reduce, to some degree, the chance that an undesirable situation like the above will occur.

However, in the case of using the protective cover disposed on the support mechanism according to the technology described in JP 2005-204898A, for example, since the imaging device is not adequately secured inside the protective cover, when a shock is imparted to the medical observation apparatus, there is a risk of the shock affecting the imaging device. Thus, for example, even if the protective cover disposed on the support mechanism according to the technology described in JP 2005-204898A is used, the imaging device provided in the medical observation apparatus is not necessarily protected adequately.

The present disclosure proposes a new and improved protective cover and medical observation apparatus capable of protecting the imaging device provided in the medical observation apparatus.

According to an embodiment of the present disclosure, there is provided a protective cover including: an installation section configured to be installed on an arm that supports an imaging device, the arm including a plurality of links joined to each other by one or a plurality of joint sections; and a protective section configured to cover the imaging device.

In addition, according to an embodiment of the present disclosure, there is provided a medical observation apparatus including: an arm including a plurality of links joined to each other by one or a plurality of joint sections; an imaging device supported by the arm; and a protective cover. The protective cover includes an installation section configured to be installed on the arm, and a protective section configured to cover the imaging device.

According to an embodiment of the present disclosure, the imaging device provided in the medical observation apparatus can be protected.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 10 is an explanatory diagram illustrating an example of the external appearance of a protective cover according to the second embodiment, and a part of the medical observation apparatus on which with the protective cover according to the second embodiment is installed.

DETAILED DESCRIPTION OF THE EMBODIMENT(S)

Figure 1:
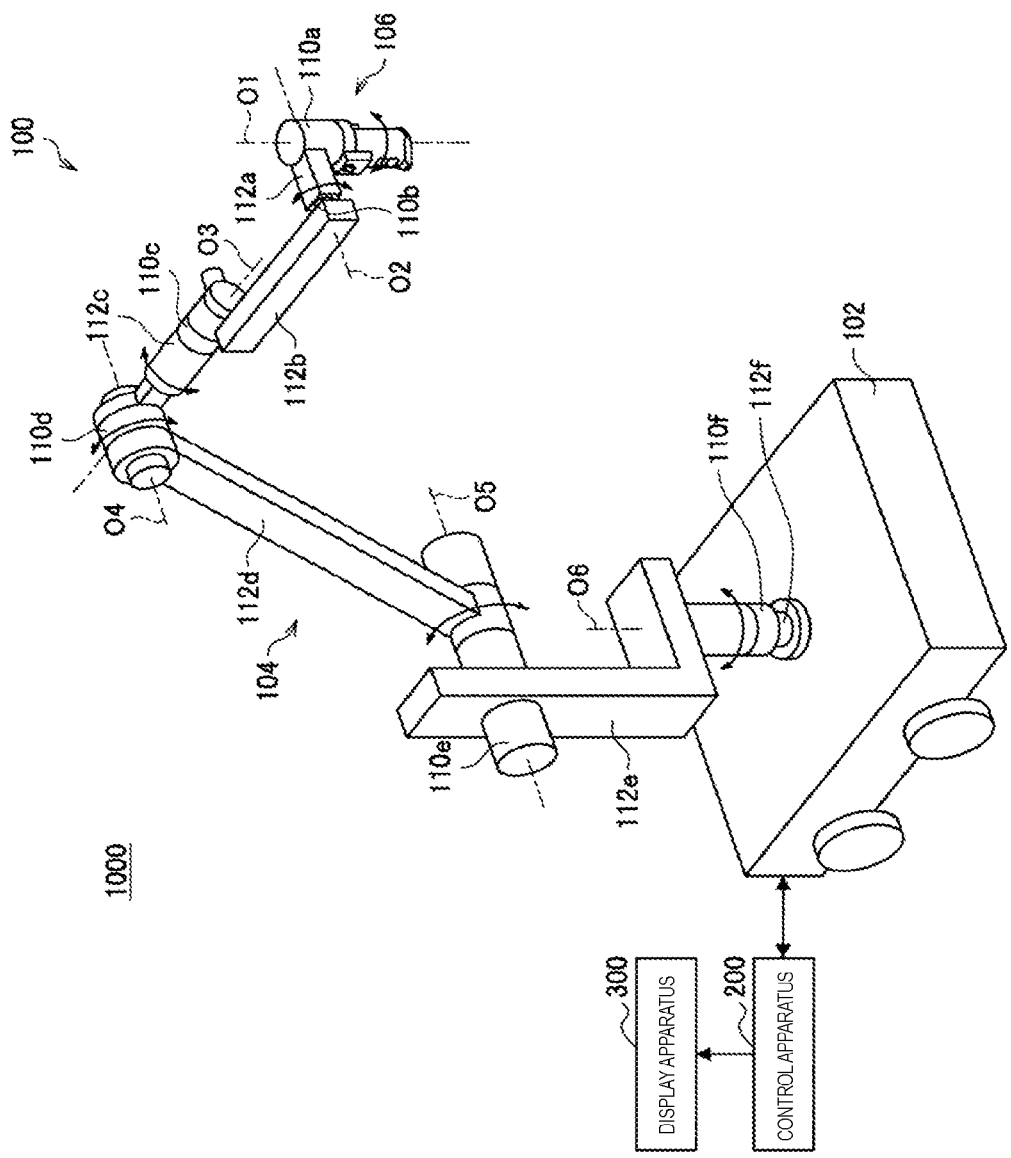
FIG. 1 is an explanatory diagram illustrating an example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment
2. Protective cover according to present embodiment Medical Observation System According to Present Embodiment Before describing an example of the configuration of a protective cover according to the present embodiment, an example of a medical observation system according to the present embodiment that includes a medical observation apparatus according to the present embodiment will be described.

[1] Configuration of Medical Observation System

FIG. 1 is an explanatory diagram illustrating an example of the configuration of a medical observation system 1000 according to the present embodiment. The medical observation system 1000 includes a medical observation apparatus 100, a control apparatus 200, and a display apparatus 300, for example.

Note that the medical observation system according to the present embodiment is not limited to the example illustrated in FIG. 1.

For example, in the medical observation system according to the present embodiment, the medical observation apparatus 100 may include the functions of the control apparatus 200. In the case in which the medical observation apparatus 100 includes the functions of the control apparatus 200, the medical observation system according to the present embodiment includes the medical observation apparatus 100 and the display apparatus 300, for example.

Additionally, the medical observation system according to the present embodiment may also be a configuration that includes a plurality of one or more from among the medical observation apparatus 100, the control apparatus 200, and the display apparatus 300.

In the case in which the medical observation system according to the present embodiment includes a plurality of the medical observation apparatus 100, the protective cover according to the present embodiment described later may be installed with respect to each medical observation apparatus 100.

Also, in the case in which the medical observation system according to the present embodiment is a configuration that includes multiple medical observation apparatuses 100 and control apparatuses 200, the medical observation apparatus 100 and the control apparatus 200 may be associated in a 1-to-1 manner, or multiple medical observation apparatuses 100 may be associated with a single control apparatus 200. In the case in which multiple medical observation apparatuses 100 are associated with a single control apparatus 200, which medical observation apparatus 100 is controlled is switched by performing a switching operation or the like in the control apparatus 200, for example.

Also, in the case in which the medical observation system according to the present embodiment is a configuration that includes multiple medical observation apparatuses 100 and display apparatuses 300, the medical observation apparatus 100 and the display apparatus 300 may be associated in a 1-to-1 manner, or multiple medical observation apparatuses 100 may be associated with a single display apparatus 300. In the case in which multiple medical observation apparatuses 100 are associated with a single display apparatus 300, which medical observation apparatus 100 provides a taken image to be displayed on a display screen is switched by performing a switching operation or the like in the display apparatus 300, for example.

[1-1] Display Apparatus 300

The display apparatus 300 is a display device in the medical observation system 1000, and corresponds to an external display device from the perspective of the medical observation apparatus 100. The display apparatus 300 displays various images on a display screen, such as a taken image (a moving image or multiple still images; the same applies hereinafter) taken in the medical observation apparatus 100, or an image related to a user interface (UI), for example. In addition, the display apparatus 300 may also be a configuration capable of 3D display. The display on the display apparatus 300 is controlled by, for example, the control apparatus 200.

In the medical observation system 1000, the display apparatus 300 is installed in an arbitrary location visible to a person involved in a surgery inside an operating room, such as on a wall, the ceiling, or the floor of the operating room, for example. Examples of the display apparatus 300 include a liquid crystal display, an organic EL display, a cathode ray tube (CRT) display, and the like.

Note that the display apparatus 300 is not limited to the example illustrated above.

For example, the display apparatus 300 may also be an arbitrary wearable apparatus that is used by being worn on the body of the surgeon or the like, such as a head-mounted display, an eyewear-type apparatus, or the like.

[1-2] Control Apparatus 200

The control apparatus 200 controls each of the operation in the medical observation apparatus 100 and the operation in the display apparatus 300. In other words, the control apparatus 200 fulfills a role of controlling the operations of the various equipment included in the medical observation system 1000.

The control apparatus 200 is provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The control apparatus 200 runs on electric power supplied from an internal power source such as a battery provided in the control apparatus 200, on electric power supplied from a connected external power source, or the like, for example.

The one or multiple processors (not illustrated) perform control-related processes on a control target such as the medical observation apparatus 100. The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) is a storage device provided in the control apparatus 200, and stores various data, such as data related to control, various applications, and the like, for example. Herein, examples of the recording medium (not illustrated) include a magnetic recording medium such as a hard disk, non-volatile memory such as flash memory, and the like. Additionally, the recording medium (not illustrated) may also be removable from the control apparatus 200.

The communication device (not illustrated) is a communication device provided in the control apparatus 200, and fulfills a role of communicating in a wireless or wired manner with an external apparatus such as the medical observation apparatus 100 and the display apparatus 300. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a radio frequency (RF) circuit (wireless communication), a local area network (LAN) terminal and a transmitting-receiving circuit (wired communication), and the like.

The control apparatus 200 may be an arbitrary piece of equipment capable of controlling the operations of the various equipment included in the medical observation system according to the present embodiment, such as a "medical controller" or a "computer such as a server", for example. Also, the control apparatus 200 may be, for example, an integrated circuit (IC) that can be embedded in equipment like the above.

To give one example of control in the control apparatus 200, on the basis of an operation with respect to the medical observation apparatus 100, for example, the control apparatus 200 causes the medical observation apparatus 100 to operate in an operating mode (described later) corresponding to the operation. Also, on the basis of an operation with respect to the medical observation apparatus 100, for example, the control apparatus 200 controls imaging in the imaging device (described later) provided in the medical observation apparatus 100. Examples of the control of the imaging according to the present embodiment include one or both of control of the zoom magnification and control of the focal length.

Also, in the case in which an image signal generated by imaging in the imaging device (described later) provided in the medical observation apparatus 100 and transmitted from the medical observation apparatus 100 is received, in the control apparatus 200, image processing on the image signal is performed by the one or multiple processors (not illustrated), for example. Examples of image processing according to the present embodiment include one or multiple processes from among various processes such as gamma correction, white balance adjustment, image enlargement or reduction related to the electronic zoom function, and pixel interpolation, for example. Note that in the medical observation system according to the present embodiment, the image processing according to the present embodiment may also be performed in the medical observation apparatus 100.

For example, the control apparatus 200 transmits a display control signal and the image signal subjected to imaging processing as above to the display apparatus 300. By transmitting the display control signal and the image signal to the display apparatus 300, on the display screen of the display apparatus 300, a taken image in which the observation target is imaged (for example, a taken image in which the operating site is imaged) is displayed enlarged or reduced at a desired magnification by one or both of the optical zoom function and the electronic zoom function.

[1-3] Medical Observation Apparatus 100

The medical observation apparatus 100 is an electronic imaging medical observation apparatus. For example, in the case in which the medical observation apparatus 100 is used during surgery, the surgeon (one example of the user of the medical observation apparatus 100) observes an operating site while referring to a taken image which has been taken by the medical observation apparatus 100 and displayed on the display screen of the display apparatus 300, and performs various treatments, such as techniques depending on the surgical procedure, on the operating site.

The medical observation apparatus 100 is provided with a base 102, an arm 104, and an imaging device 106, for example.

In addition, although not illustrated in FIG. 1, the medical observation apparatus 100 may also be provided with a communication device (not illustrated) that communicates according to a communication scheme supported by a communication device (not illustrated) provided in the control apparatus 200, for example. Note that in the case in which the imaging device 106 and the control apparatus 200 are connected in a wired manner, for example, the medical observation apparatus 100 may take a configuration not provided with a separate communication device (not illustrated). The medical observation apparatus 100 runs on electric power supplied from an internal power source such as a battery provided in the medical observation apparatus 100, on electric power supplied from a connected external power source, or the like, for example.

[1-3-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-3-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110a, 110b, 110c, 110d, 110e, and 110f, and multiple links 112a, 112b, 112c, 112d, 112e, and 112f rotatably joined to each other by the joint sections 110a, 110b, 110c, 110d, 110e, and 110f. The rotatable range of each of the joint sections 110a, 110b, 110c, 110d, 110e, and 110f is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first 7 axis O1, second axis O2, third axis O3, fourth axis O4, fifth axis O5, and sixth axis O6) corresponding to the six joint sections 110a, 110b, 110c, 110d, 110e, and 110f included in the arm 104. More specifically, in the medical observation apparatus 100 illustrated in FIG. 1, motion with six degrees of freedom, including three degrees of translational freedom and three degrees of rotational freedom, is realized.

The joint section 110a has an approximately cylindrical shape, and supports the imaging device 106 (the top end of the imaging device 106 in FIG. 1) on the front end portion of the joint section 110a (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the taken image taken by the imaging device 106 becomes an image which has changed so that the field of view rotates.

The link 112a is an approximately rod-shaped member, and securely supports the joint section 110a. The link 112a extends in a direction orthogonal to the first axis O1, for example, and is connected to the joint section 110b.

The joint section 110b has an approximately cylindrical shape, and supports the link 112a so as to allow revolution about a rotation axis (second axis O2) orthogonal to the first axis O1. Also, the link 112b is securely connected to the joint section 110b.

The link 112b is an approximately rod-shaped member, and extends in a direction orthogonal to the second axis O2. Also, each of the joint section 110b and the joint section 110c is connected to the link 112b.

The joint section 110c has an approximately cylindrical shape, and supports the link 112b so as to allow revolution about a rotation axis (third axis O3) mutually orthogonal to each of the first axis O1 and the second axis O2. Also, one end of the link 112c is securely connected to the joint section 110c.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the taken image in a flat plane.

The link 112c is a member in which one end has an approximately cylindrical shape, and the other end has an approximately rod-like shape. On the side of the one end of the link 112c, the joint section 110c is securely connected so that the central axis of the joint section 110c and the central axis of the approximately cylindrical shape are the same. Also, on the side of the other end of the link 112c, the joint section 110d is connected.

The joint section 110d has an approximately cylindrical shape, and supports the link 112c so as to allow revolution about a rotation axis (fourth axis O4) orthogonal to the third axis O3. The link 112d is securely connected to the joint section 110d.

The link 112d is an approximately rod-shaped member, and extends orthogonally to the fourth axis O4. One end of the link 112d is securely connected to the joint section 110d so as to abut the approximately cylindrical side face of the joint section 110d. Also, the joint section 110e is connected to the other end of the link 112d (the end on the opposite side of the side where the joint section 110d is connected).

The joint section 110e has an approximately cylindrical shape, and supports one end of the link 112d so as to allow revolution about a rotation axis (fifth axis O5) parallel to the fourth axis O4. Also, one end of the link 112e is securely connected to the joint section 110e.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112e is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110e is securely connected to the part of the first member of the link 112e that extends in the vertical direction. Also, the joint section 110f is connected to the second member of the link 112e.

The joint section 110f has an approximately cylindrical shape, and supports the link 112e so as to allow revolution about a rotation axis (sixth axis O6) parallel to the vertical direction. Also, the link 112f is securely connected to the joint section 110f.

The link 112f is an approximately rod-shaped member, and extends in the vertical direction. The joint section 110f is connected to one end of the link 112f. Also, the other end of the link 112f (the end on the opposite side of the side where the joint section 110f is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110a, 110b, 110c, 110d, 110e, and 110f of the arm 104 may be provided with a brake that restrains rotation in each of the joint sections 110a, 110b, 110c, 110d, 110e, and 110f. The brake according to the present embodiment may be a brake of an arbitrary method, such as a mechanically driven brake or an electrically driven electromagnetic brake, for example.

The driving of the above brakes is controlled by the control apparatus 200. By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-3-3] Imaging Device 106

The imaging device 106 is supported by the arm 104, and images an observation target such as an operating site of a patient, for example. Imaging in the imaging device 106 is controlled by, for example, the control apparatus 200.

The imaging device 106 has a configuration corresponding to an electronic imaging microscope, for example.

Figure 2:
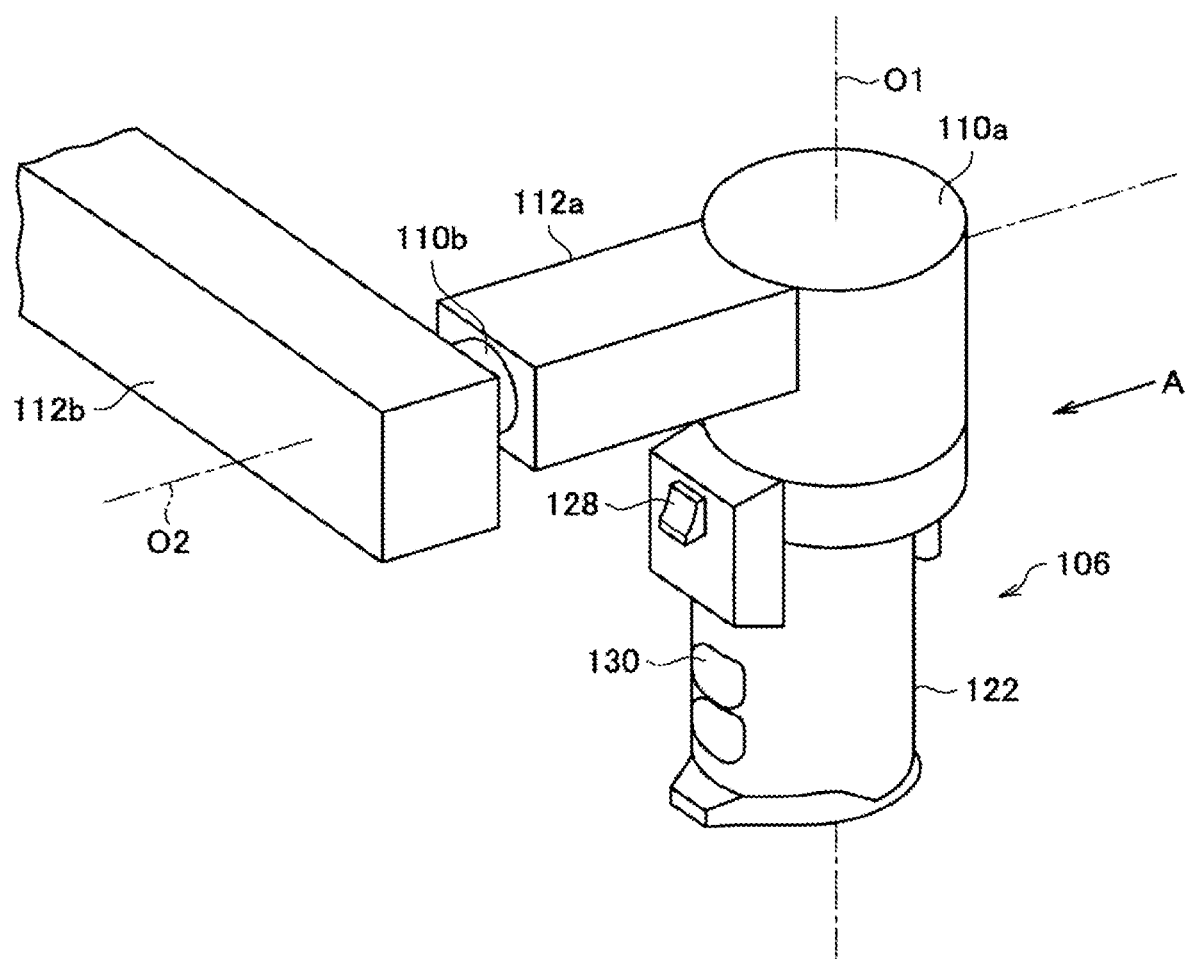
FIG. 2 is an explanatory diagram for explaining an example of the configuration of an imaging device provided in a medical observation apparatus according to the present embodiment.
Figure 3:
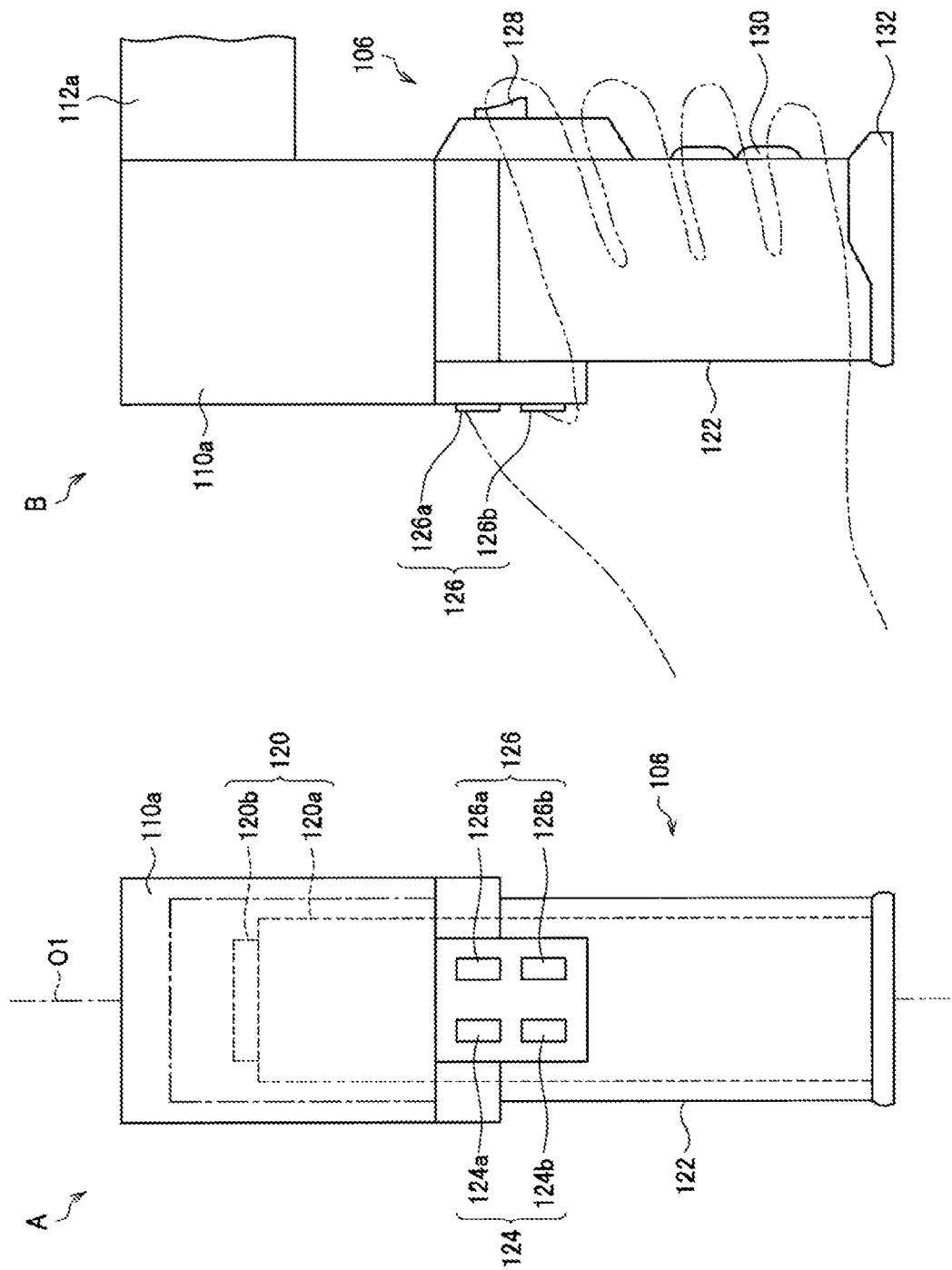
FIG. 3 is an explanatory diagram for explaining an example of the configuration of an imaging device provided in a medical observation apparatus according to the present embodiment.

FIGS. 2 and 3 are explanatory diagrams for explaining an example of the configuration of the imaging device 106 provided in the medical observation apparatus 100 according to the present embodiment. An example of the configuration of the imaging device 106 will be described with reference to FIGS. 2 and 3.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIGS. 2 and 3), for example, a cover glass (not illustrated) for protecting the imaging member 120 is provided.

Additionally, for example, a light source (not illustrated) is provided inside the barrel unit 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a taken image) is obtained by the imaging member 120.

As the imaging member 120, any of various known types of configurations used in an electronic imaging microscope section can be applied.

To give one example, the imaging member 120 includes an optical system 120a and an image sensor 120b including an imaging element that takes an image of an observation target with light transmitted through the optical system 120a, for example. The optical system 120a includes optical elements such as a mirror and one or multiple lenses, such as an objective lens, a zoom lens, and a focus lens, for example. Examples of the image sensor 120b include an image sensor using multiple imaging elements, such as a complementary metal-oxide semiconductor (CMOS) or a charge-coupled device (CCD).

The imaging member 120 may also include a pair of imaging elements, or in other words, be configured to function as what is called a stereo camera. The imaging member 120 is equipped with one or multiple functions typically provided in an electronic imaging microscope section, including at least a zoom function (one or both of an optical zoom function and an electronic zoom function), such as an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 300 having a large display screen, such as 50 inches or more, for example. For this reason, visibility is improved for the surgeon watching the display screen. Also, by configuring the imaging member 120 to be capable of imaging at high resolutions, even if the taken image is enlarged by the electronic zoom function and displayed on the display screen of the display apparatus 300, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIGS. 2 and 3, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIGS. 2 and 3.

The zoom switch 124 and the focus switch 126 are an example of an operating device for adjusting the imaging parameters in the imaging device 106.

The zoom switch 124 includes, for example, a zoom-in switch 124a that increases the zoom magnification (enlargement ratio), and a zoom-out switch 124b that decreases the zoom magnification. By performing an operation on the zoom switch 124, the zoom magnification is adjusted, and the zoom is adjusted.

The focus switch 126 includes, for example, a long-range focus switch 126a that increases the focal length to the observation target (subject), and a close-range focus switch 126b that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120a when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the 132 is provided obviously are not limited to the example illustrated in FIGS. 2 and 3. In addition, the imaging device 106 does not have to be provided with one or both of the anti-slip member 130 and the projecting member 132.

The image signal generated by imaging in the imaging device 106 is transmitted to the control apparatus 200, for example, and as described above, in the control apparatus 200, various types of image processing are performed on the image signal.

The medical observation apparatus 100 includes the configuration illustrated with reference to FIGS. 1 to 3, for example.

Note that the configuration of the medical observation apparatus according to the present embodiment is not limited to the configuration illustrated with reference to FIGS. 1 to 3.

For example, although FIG. 1 illustrates an example configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 2 and 3 illustrate an example in which various types of operating devices for controlling the operation of the imaging device 106 are provided on the imaging device 106, some or all of the operating devices illustrated in FIGS. 2 and 3 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a remote controller or a footswitch.

Additionally, as described above, the medical observation apparatus according to the present embodiment may also include the functions of the control apparatus 200. In the case in which the functions of the control apparatus 200 are included, the medical observation apparatus according to the present embodiment is provided with a processor such as an MPU, and in the processor, various processes for realizing the functions of the control apparatus 200 are performed.

Protective Cover According to Present Embodiment

[I] Summary of Protective Cover According to Present Embodiment

Figure 4:
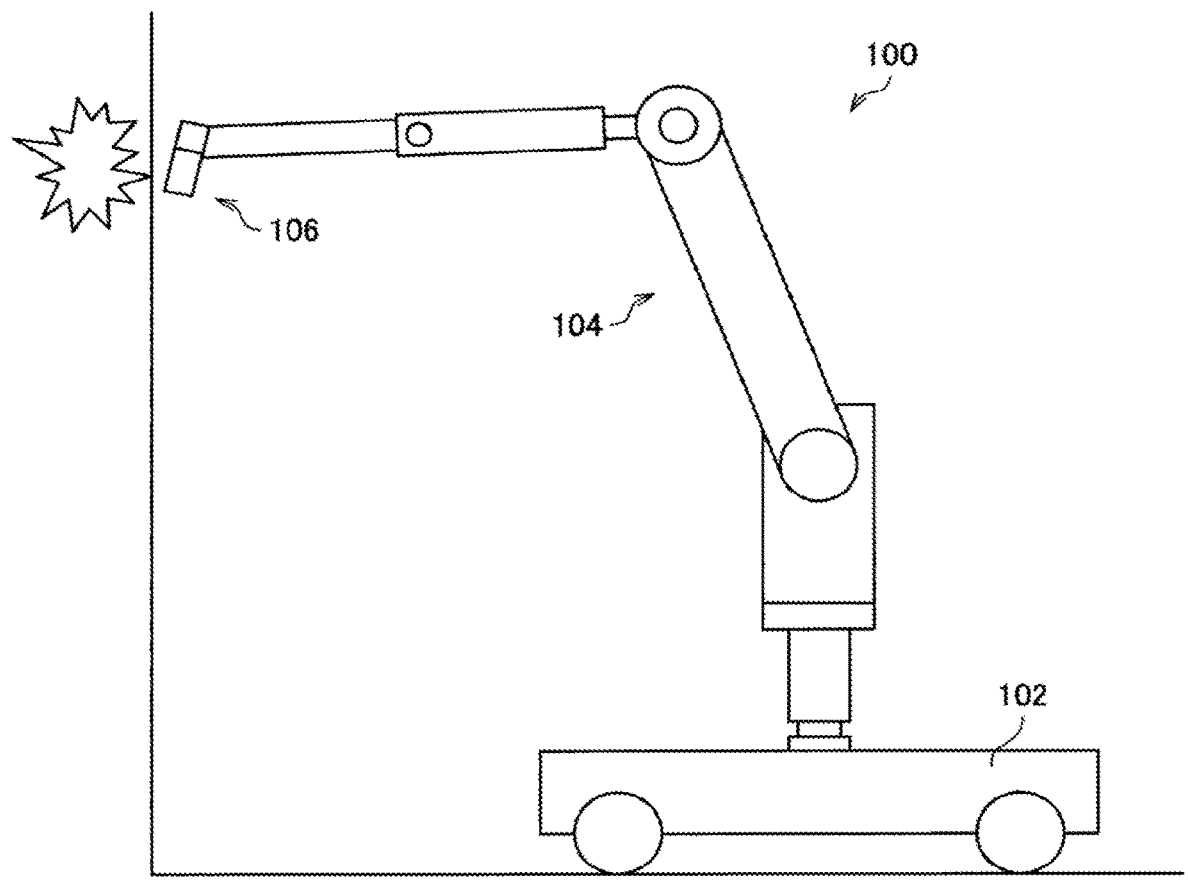
FIG. 4 is an explanatory diagram illustrating an example of a case in which the imaging device collides with a wall when the medical observation apparatus illustrated in FIG. 1 is moved.

FIG. 4 is an explanatory diagram illustrating an example of a case in which the imaging device 106 collides with a wall when the medical observation apparatus 100 illustrated in FIG. 1 is moved.

The imaging device 106 provided in the medical observation apparatus 100 includes a precise mechanism for improving the observation performance, and moreover, fine optical adjustments are performed in the imaging device 106. For this reason, like in the case illustrated in FIG. 4, if the imaging device 106 collides with a wall or the like when the medical observation apparatus 100 is moved, the mechanism included in the imaging device 106 may suffer damage due to the shock of colliding with the wall or the like, and an undesirable situation may occur, such as the imaging device 106 ceasing to function normally.

Accordingly, the present embodiment proposes a protective cover capable of protecting the imaging device provided in the medical observation apparatus.

The protective cover according to the present embodiment is installed on the arm that supports the imaging device, the arm including multiple links joined to each other by joint sections. In other words, when installed on the medical observation apparatus, the protective cover according to the present embodiment is supported by the arm included in the medical observation apparatus.

Also, when installed on the arm included in the medical observation apparatus, the protective cover according to the present embodiment covers the imaging device included in the medical observation apparatus. The protective cover according to the present embodiment covers all of the imaging device included in the medical observation apparatus, or a part of the imaging device included in the medical observation apparatus.

Herein, states in which the imaging device is covered by the protective cover according to the present embodiment include, for example, a state in which a gap is provided between the protective cover and the imaging device, and a state in which a gap is not provided between the protective cover and the imaging device. Note that the first embodiment and the second embodiment described later illustrate the case in which the state of the imaging device being covered by the protective cover is the state in which a gap is provided between the protective cover and the imaging device.

As above, the protective cover according to the present embodiment is installed on the arm included in the medical observation apparatus, and covers the imaging device included in the medical observation apparatus.

Thus, even if the imaging device portion hypothetically collides with a wall or the like when the imaging device is moved, since the imaging device is covered by the protective cover according to the present embodiment, the shock is prevented from being imparted directly to the imaging device.

Consequently, the protective cover according to the present embodiment is able to protect the imaging device provided in the medical observation apparatus.

Also, in the medical observation apparatus on which the protective cover according to the present embodiment is installed, an undesirable situation, such as the imaging device ceasing to function normally due to a shock, is prevented from occurring. Furthermore, by preventing the occurrence of an undesirable situation like the above, the frequency at which repair or replacement of the medical observation apparatus may be required is reduced further.

Also, when installed on the medical observation apparatus, the protective cover according to the present embodiment covers the imaging device included in the medical observation apparatus in a state in which the medical observation apparatus is supported by the arm, and thus the positional relationship between the protective cover according to the present embodiment and the imaging device is kept constant, irrespectively of the state of the arm.

Consequently, the protective cover according to the present embodiment is able to protect the imaging device provided in the medical observation apparatus more reliably than a protective cover disposed on the support mechanism according to the technology described in JP 2005-204898A, for example.

The following, by taking the medical observation apparatus 100 included in the medical observation system 1000 as an example, describes an example of the configuration of the protective cover according to the present embodiment, and a medical observation apparatus on which the protective cover according to the present embodiment is installed.

[II] Protective Cover According to First Embodiment

Figure 5:
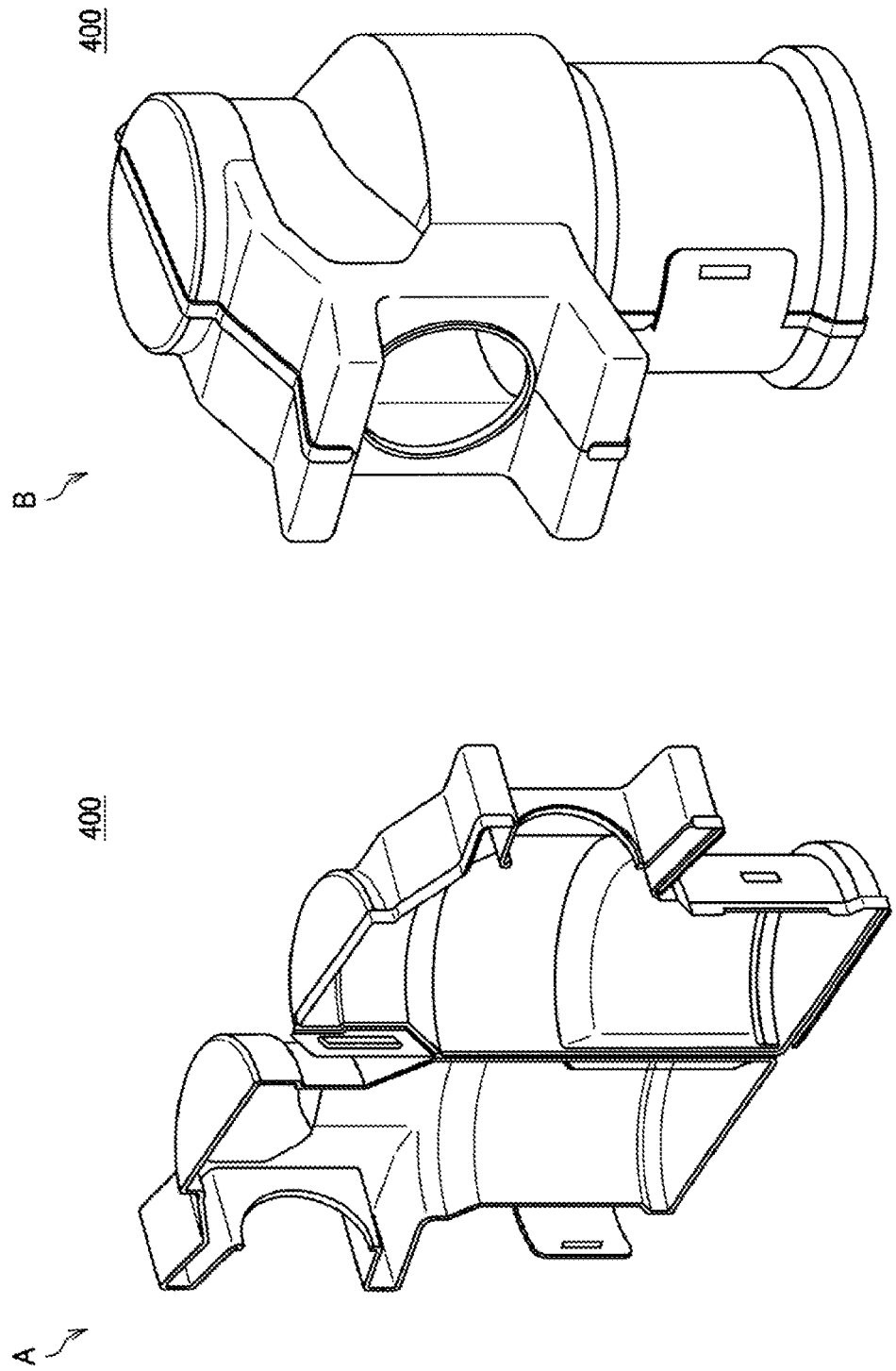
FIG. 5 is an explanatory diagram illustrating an example of the external appearance of a protective cover according to the first embodiment.

FIG. 5 is an explanatory diagram illustrating an example of the external appearance of a protective cover 400 according to the first embodiment, and illustrates an example of a protective cover applicable to the medical observation apparatus 100 illustrated in FIG. 1. A of FIG. 5 illustrates an example of the external appearance of the protective cover 400 in an open state, in which the protective cover 400 is opened for installation on the medical observation apparatus 100. B of FIG. 5 illustrates an example of the protective cover 400 in an installed state when installed on the medical observation apparatus 100.

Note that the shape of the protective cover according to the first embodiment is not limited to the example illustrated in FIG. 5. For example, it is possible for the protective cover according to the first embodiment to have the shape of the arm provided in the medical observation apparatus according to the present embodiment (the shape of the link on which the protective cover is installed) or a shape corresponding to the shape of the imaging device provided in the medical observation apparatus according to the present embodiment.

Figure 6:
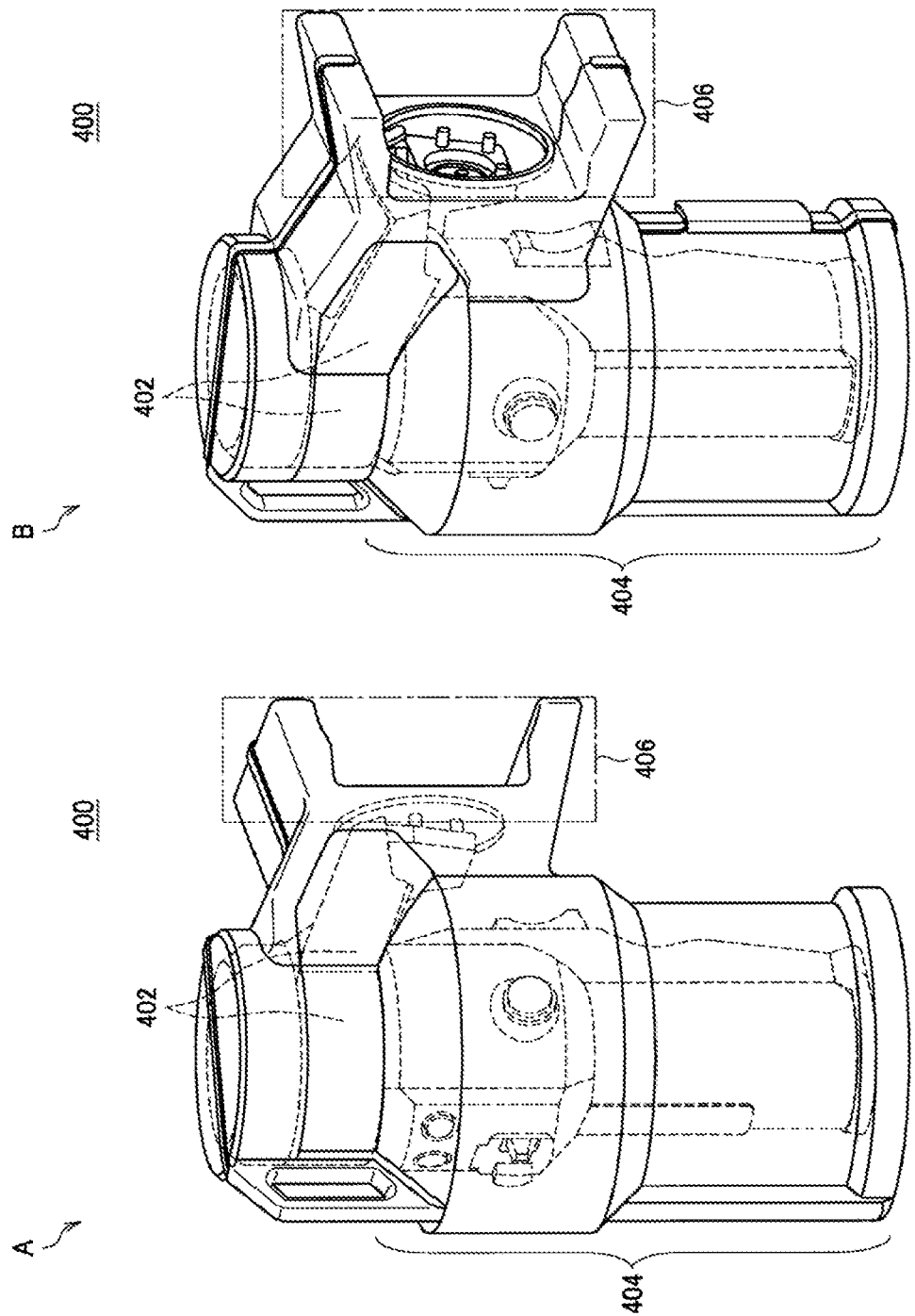
FIG. 6 is an explanatory diagram illustrating a part of the medical observation apparatus on which the protective cover according to the first embodiment is installed.

FIG. 6 is an explanatory diagram illustrating a part of the medical observation apparatus 100 on which the protective cover 400 according to the first embodiment is installed.

The protective cover 400 is provided with an installation section 402, a protective section 404, and an installation restraint section 406.

Herein, the protective cover 400 is formed with an arbitrary material, such as polypropylene or polyurethane, for example, able to alleviate shocks imparted to the imaging device 106 when installed on the medical observation apparatus 100.

Also, the protective cover 400 may be formed in an integrated manner, or may be multiple members connected by an arbitrary method, such as by being glued with an adhesive. In other words, the installation section 402, the protective section 404, and the installation restraint section 406 may be formed by a single member, or may be formed by multiple members.

The installation section 402 is installed on the arm 104 that supports the imaging device 106. More specifically, the installation section 402 is installed on the link 112a to which the imaging device 106 is joined (an example of the first link to which the imaging device is joined) from among the multiple links included in the arm 104. In other words, the protective cover 400, in which the installation section 402 is installed on the arm 104, is supported by the link 112a included in the arm 104.

The protective section 404 covers all of the imaging device 106. By having the protective section 404 cover all of the imaging device 106, even if a shock is imparted to any portion of the imaging device 106, the shock is prevented from being imparted directly to the imaging device 106.

Herein, the imaging device 106 covered by the protective section 404 may also be rotatable about the optical axis in the imaging device 106. Herein, in the medical observation apparatus 100 illustrated in FIG. 1, for example, the optical axis in the imaging device 106 is aligned with the first axis O1. In other words, the imaging device 106 covered by the protective section 404 may also be rotatable about the first axis O1.

In the medical observation apparatus 100 on which the protective cover 400 is installed, being rotatable about the optical axis in the imaging device 106 is realized by, for example, "designing the protective section 404 so that the internal space of the protective section 404 is larger than the maximum rotation path of the imaging device 106 about the first axis O1".

As above, by having the imaging device 106 covered by the protective section 404 be rotatable about the optical axis, the person who installs the protective cover 400 on the medical observation apparatus 100 is not required to align the position of the imaging device 106 about the first axis O1. Consequently, by having the imaging device 106 covered by the protective section 404 be rotatable about the optical axis, convenience can be improved further for the person who installs the protective cover 400 on the medical observation apparatus 100.

The installation restraint section 406 is a member that enables the installation of the installation section 402 on the arm 104 when the imaging device 106 and the arm 104 are in a specific positional relationship. In other words, the installation restraint section 406 is a member that regulates the attitude of the imaging device 106 with respect to the arm 104 in the medical observation apparatus 100. The installation restraint section 406 has, for example, a configuration that clasps the link 112b (an example of a second link joined to the first link to which the imaging device is joined), and by clasping the link 112b, restrains the attitude of the imaging device 106 with respect to the arm 104.

More specifically, the installation restraint section 406 enables the installation of the installation section 402 on the arm 104 when the positional relationship between the imaging device and the link 112b (an example of a second link joined to the first link to which the imaging device is joined) from among the multiple links included in the arm 104 is a specific positional relationship.

The position of the imaging device 106 with respect to the link 112b is determined by the second axis O2 in the arm 104. In other words, the installation restraint section 406 fulfills a role of disallowing installation unless the imaging device 106 is in a specific position about the second axis O2 with respect to the link 112b.

Examples of cases in which the positional relationship between the imaging device 106 and the link 112b are in a specific positional relationship when the protective cover 400 is used include a case in which the position of the imaging device 106 about the second axis O2 with respect to the link 112b is the position illustrated in FIG. 1.

Herein, the specific positional relationship according to the present embodiment may change depending on how the shape of the installation restraint section 406 is set. For example, the shape of the installation restraint section 406 is set so that the imaging device 106 does not become the most prominent part when the arm 104 included in the medical observation apparatus 100 is in a predetermined storage state.

By setting the installation restraint section 406 with the shape illustrated in FIG. 6, for example, when the medical observation apparatus 100 moves while the arm 104 is in the predetermined storage state, regulation of the attitude of the imaging device 106 at a position where the imaging device 106 does not stick out the most is realized.

Figure 7:
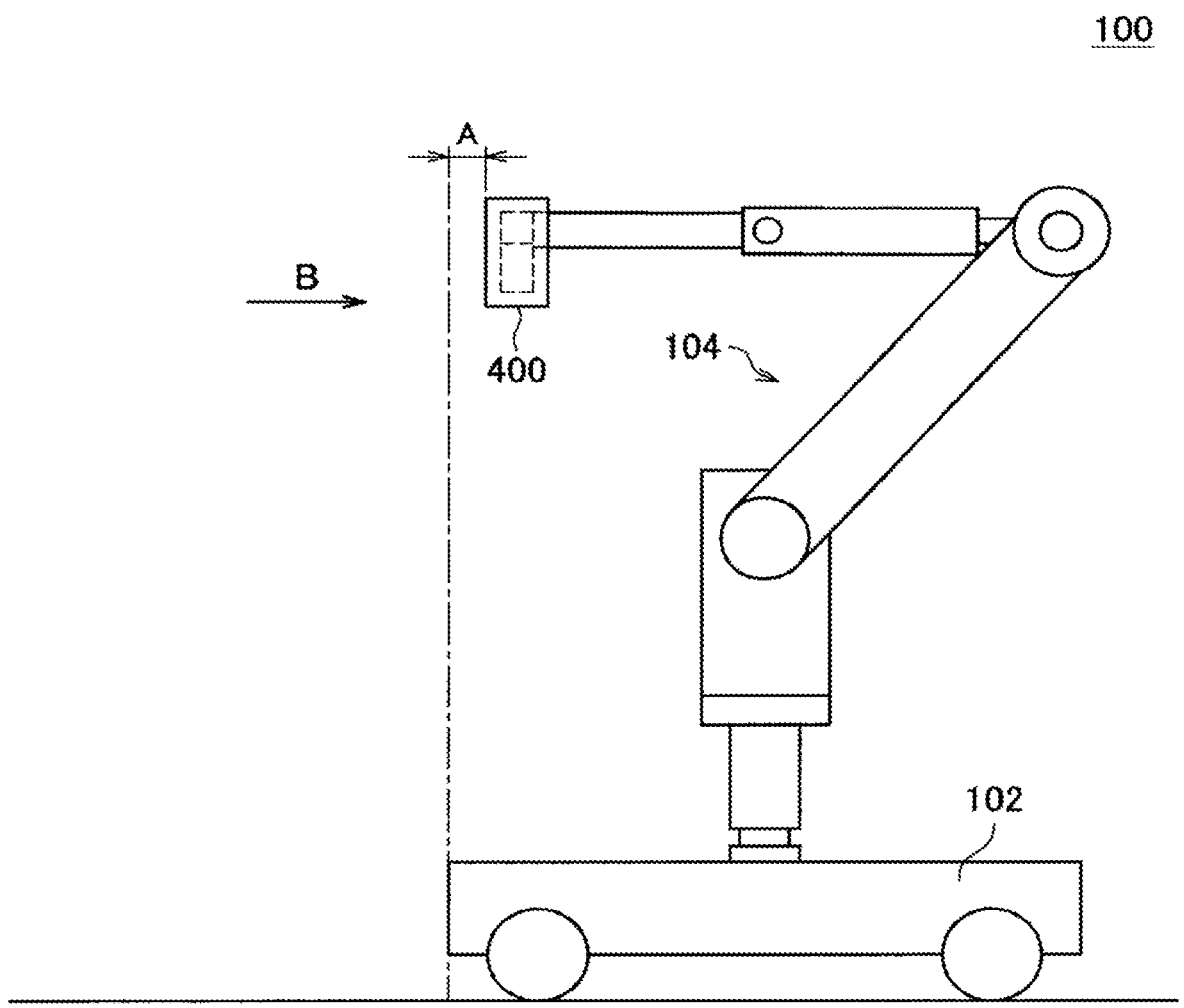
FIG. 7 is an explanatory diagram illustrating an example of a case in which the medical observation apparatus on which the protective cover according to the first embodiment is installed is in a predetermined storage state.
Figure 8:
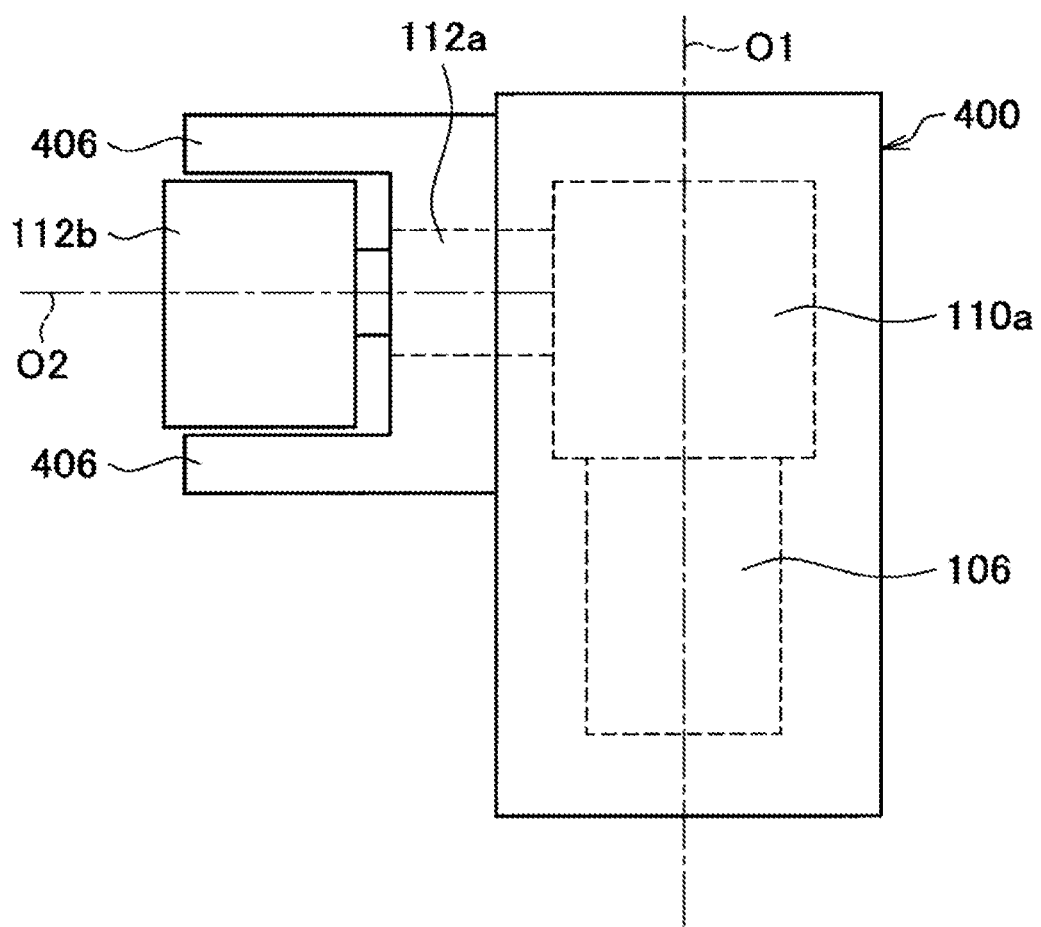
FIG. 8 is an explanatory diagram illustrating a part of the medical observation apparatus on which the protective cover according to the first embodiment is installed.

FIG. 7 is an explanatory diagram illustrating an example of a case in which the medical observation apparatus 100 on which the protective cover 400 according to the first embodiment is installed is in the predetermined storage state. FIG. 8 is an explanatory diagram illustrating the part of the medical observation apparatus 100 on which the protective cover 400 according to the first embodiment is installed, and corresponds to a schematic arrow view from the B direction illustrated in FIG. 7.

The case in which the medical observation apparatus 100 is in the predetermined storage state may be a state in which the arm 104 is folded up as illustrated in FIG. 7, for example.

In the case of being in the predetermined storage state as illustrated in FIG. 7, in the medical observation apparatus 100 on which the protective cover 400 is installed, the imaging device 106 covered by the protective cover 400 does not become the most prominent part, as indicated by the sign A in FIG. 7.

Thus, hypothetically, in the case in which the medical observation apparatus 100 on which the protective cover 400 is installed is moved while in the predetermined storage state as illustrated in FIG. 7, even if the medical observation apparatus 100 collides with a wall or the like, the imaging device 106 covered by the protective cover 400 does not collide directly with the wall or the like. Consequently, even if the medical observation apparatus 100 collides with a wall or the like as above, the shock imparted to the imaging device 106 is decreased further, and thus the possibility that an undesirable situation may occur, such as the imaging device 106 ceasing to function normally, is reduced further.

Also, as illustrated in FIG. 8, the protective cover 400 is installed on the medical observation apparatus 100 so that the installation restraint section 406 clasps the link 112b of the medical observation apparatus 100. At this time, as illustrated in FIG. 8, the attitude of the imaging device 106 is restrained so that the rotation axis (first axis O1) parallel to the central axis of the imaging device 106 is the vertical direction (or a nearly vertical direction). For example, by restraining the attitude of the imaging device 106 with the installation restraint section 406 as illustrated in FIG. 8, it is possible to further decrease the "possibility of the imaging device 106 colliding with an obstacle such as a wall in the case in which the medical observation apparatus 100 on which the protective cover 400 is installed is moved in the predetermined storage state." Note that the configuration of the installation restraint section 406 and the attitude of the imaging device 106 restrained by the installation restraint section 406 obviously are not limited to the example illustrated in FIG. 8.

The protective cover 400 according to the first embodiment has the configuration illustrated in FIG. 6, for example.

Herein, the protective cover 400 is installed on the arm 104 included in the medical observation apparatus 100, and covers the imaging device 106 included in the medical observation apparatus 100.

Consequently, the protective cover 400 is able to protect the imaging device 106 provided in the medical observation apparatus 100.

Also, the protective cover 400 is able to exhibit the effects indicated in the summary of the protective cover according to the present embodiment described earlier.

Note that the configuration of the protective cover 400 according to the first embodiment is not limited to the configuration indicated with reference to FIG. 6.

For example, the installation section 402 of the protective cover 400 may also be provided with a cushioning member in the portion that contacts the arm 104 when installed on the arm 104 included in the medical observation apparatus 100. Examples of the cushioning member according to the present embodiment include a member formed with an arbitrary material, such as rubber, for example, capable of alleviating external forces imposed on the imaging device 106.

Figure 9:
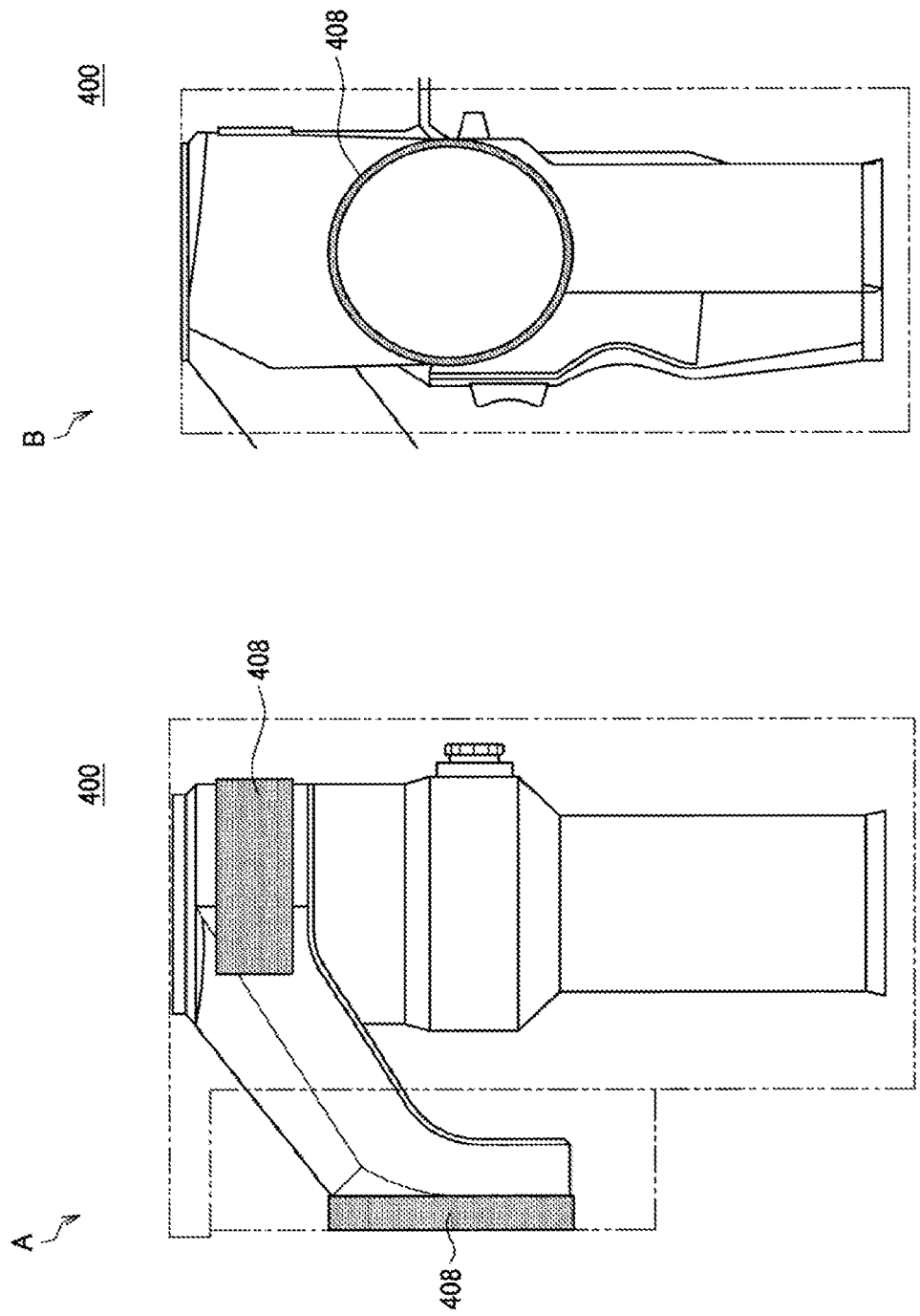
FIG. 9 is an explanatory diagram illustrating another example of the configuration of the protective cover according to the first embodiment.

FIG. 9 is an explanatory diagram for explaining another example of the configuration of the protective cover 400 according to the first embodiment, and illustrates a part of the medical observation apparatus 100 on which the protective cover 400 provided with the a cushioning member 408 is installed. A of FIG. 9 schematically illustrates a side view of the part of the medical observation apparatus 100 on which the protective cover 400 is installed, while B of FIG. 9 schematically illustrates a top view of the part of the medical observation apparatus 100 on which the protective cover 400 is installed.

For example, as illustrated in FIG. 9, the cushioning member 408 is provided on each of the contacting portions that contact the link 112a when the protective cover 400 is installed on the medical observation apparatus 100. Note that the cushioning member 408 may also be provided on some of the contacting portions that contact the link 112a when the protective cover 400 is installed on the medical observation apparatus 100.

By providing the installation section 402 with the cushioning member 408, in the case in which the imaging device 106 covered by the protective section 404 of the protective cover 400 collides with a wall or the like, the shock imparted to the imaging device 106 can be decreased further than the protective cover 400 described with reference to FIG. 6.

In addition, the protective cover according to the first embodiment may take a configuration not provided with the installation restraint section 406.

Even with a configuration not provided with the installation restraint section 406, the protective cover according to the first embodiment can be installed on the arm 104 included in the medical observation apparatus 100, and is able to cover the imaging device 106 included in the medical observation apparatus 100. Thus, even with a configuration not provided with the installation restraint section 406, the protective cover according to the first embodiment is able to protect the imaging device 106 provided in the medical observation apparatus 100.

Additionally, the protective cover according to the first embodiment may be a configuration provided with a protective section that covers a part of the imaging device 106 included in the medical observation apparatus 100. The protective section that covers a part of the imaging device 106 will be described in the second embodiment described later.

[III] Protective Cover According to Second Embodiment

FIG. 10 is an explanatory diagram illustrating an example of the external appearance of a protective cover 500 according to the second embodiment, and a part of the medical observation apparatus 100 on which with the protective cover 500 according to the second embodiment is installed. A of FIG. 10 illustrates an example of the external appearance of the protective cover 500, while B of FIG. 10 illustrates a part of the medical observation apparatus 100 on which the protective cover 500 is installed.

Note that the shape of the protective cover according to the second embodiment is not limited to the example illustrated in FIG. 10. For example, it is possible for the protective cover according to the second embodiment to have the shape of the arm provided in the medical observation apparatus according to the present embodiment (the shape of the link on which the protective cover is installed) or a shape corresponding to the shape of the imaging device provided in the medical observation apparatus according to the present embodiment.

The protective cover 500 is provided with an installation section 502 and a protective section 504, for example.

Herein, the protective cover 500 is formed with an arbitrary material, such as polypropylene, polyurethane, or metal, for example, able to alleviate shocks imparted to the imaging device 106 when installed on the medical observation apparatus 100.

Also, the protective cover 500 may be formed in an integrated manner, or may be multiple members connected by an arbitrary method, such as by being glued with an adhesive, or welded. In other words, the installation section 502 and the protective section 504 may be formed by a single member, or may be formed by multiple members.

The installation section 502 is installed on the arm 104 that supports the imaging device 106. More specifically, the installation section 502 is installed on the link 112*b* (an example of the second link) joined to the link 112*a* (an example of the first link) to which the imaging device 106 is joined, from among the multiple links included in the arm 104. In other words, the protective cover 500, in which the installation section 502 is installed on the arm 104, is supported by the link 112*b* included in the arm 104.

The protective section 504 covers a part of the imaging device 106. The way in which the protective section 504 covers the imaging device 106, or in other words, the shape and size of the protective section 504, may be set arbitrarily during the design or manufacture of the protective cover 500 to account for factors such as the direction of shock imparted to the imaging device 106 which is anticipated when the medical observation apparatus 100 is moved, for example.

By having the protective section 504 cover a part of the imaging device 106, the possibility of shock being directly imparted to the imaging device 106 is further reduced.

Herein, the imaging device 106 covered by the protective section 504 may also be rotatable about the optical axis in the imaging device 106. In other words, the imaging device 106 covered by the protective section 504 may also be rotatable about the first axis O1.

In the medical observation apparatus 100 on which the protective cover 500 is installed, being rotatable about the optical axis in the imaging device 106 is realized by, for example, "designing the protective section 504 so that the position of the protective section 504 with respect to the imaging device 106 when installed on the protective cover 500 is on the outward side of the maximum rotation path of the imaging device 106 about the first axis O1".

As above, by having the imaging device 106 covered by the protective section 504 be rotatable about the optical axis, the person who installs the protective cover 500 on the medical observation apparatus 100 is not required to align the position of the imaging device 106 about the first axis O1. Consequently, by having the imaging device 106 covered by the protective section 504 be rotatable about the optical axis, convenience can be improved further for the person who installs the protective cover 500 on the medical observation apparatus 100.

The protective cover 500 according to the second embodiment has the configuration illustrated in FIG. 10, for example.

Herein, the protective cover 500 is installed on the arm 104 included in the medical observation apparatus 100, and covers the imaging device 106 included in the medical observation apparatus 100.

Consequently, the protective cover 500 is able to protect the imaging device 106 provided in the medical observation apparatus 100.

Also, the protective cover 500 is able to exhibit the effects indicated in the summary of the protective cover according to the present embodiment described earlier.

Note that the configuration of the protective cover 500 according to the second embodiment is not limited to the configuration indicated with reference to FIG. 10.

For example, the installation section 502 of the protective cover 500 may also be provided with a cushioning member in the portion that contacts the arm 104 when installed on the arm 104 included in the medical observation apparatus 100.

By providing the installation section 502 with the cushioning member, in the case in which the imaging device 106 covered by the protective section 504 of the protective cover 500 collides with a wall or the like, the shock imparted to the imaging device 106 can be decreased further than the protective cover 500 described with reference to FIG. 10.

Additionally, the protective cover according to the second embodiment may be a configuration provided with a protective section that covers all of the imaging device 106 included in the medical observation apparatus 100. By providing a protective section that covers all of the imaging device 106, similarly to the protective cover 400 according to the first embodiment described above, even if a shock is imparted to any portion of the imaging device 106, the shock is prevented from being imparted directly to the imaging device 106.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A protective cover including:
an installation section configured to be installed on an arm that supports an imaging device, the arm including a plurality of links joined to each other by one or a plurality of joint sections; and
a protective section configured to cover the imaging device.

(2) The protective cover according to (1), in which
the protective cover, in which the installation section is installed on the arm, is supported by the arm.

(3) The protective cover according to (1) or (2), in which
the installation section is installed on a first link to which the imaging device is joined from among the plurality of links.

(4) The protective cover according to (3), further including:
an installation restraint section configured to enable installation of the installation section on the arm when a positional relationship between the imaging device and a second link joined to the first link among the plurality of links is a specific positional relationship.

(5) The protective cover according to (1) or (2), in which
the installation section is installed on a second link joined to a first link to which the imaging device is joined from among the plurality of links.

(6) The protective cover according to any one of (1) to (5), in which
the protective section covers all of the imaging device.

(7) The protective cover according to any one of (1) to (5), in which
the protective section covers a part of the imaging device.

(8) The protective cover according to any one of (1) to (7), in which
the imaging device covered by the protective section is rotatable about an optical axis in the imaging device.

(9) The protective cover according to any one of (1) to (8), in which
the installation section is provided with a cushioning member on a portion that contacts the arm when installed on the arm.

(10) A medical observation apparatus including:
an arm including a plurality of links joined to each other by one or a plurality of joint sections;
an imaging device supported by the arm; and
a protective cover, in which
the protective cover includes
an installation section configured to be installed on the arm, and
a protective section configured to cover the imaging device.

(11) The medical observation apparatus according to (10), in which
when the arm is in a predetermined storage state, a most prominent part of the medical observation apparatus is not the imaging device covered by the protective cover.

What is claimed is:

1. A protective cover comprising:
a first cover section configured to hold at least a part of an arm that is connected to and supports an imaging device and includes a plurality of links joined to each other by one or a plurality of joint sections; and
a second cover section configured to cover the imaging device, the second cover section being continuously connected to the first cover section, wherein
an opening through which the arm passes is provided on the first cover section,
a protrusion configured to restrain a movement of a link of the plurality of the links joined to the held part of the arm is provided adjacent to the opening,
the first cover section and the second cover section in combination form a cylindrical hollow space for accommodating the part of the arm and the imaging device,
the first cover section and the second cover section extend in a longitudinal direction of the imaging device that is parallel to an optical axis of the imaging device,
the opening is provided on a lateral side of the first cover section, and
the protrusion is provided on the lateral side of the first cover section and adjacent to the opening.

2. The protective cover according to claim 1, wherein the first cover section is configured to hold a first link to which the imaging device is joined from among the plurality of links.

3. The protective cover according to claim 2, wherein the protrusion is configured to enable installation of the first cover section on the arm when a positional relationship between the imaging device and a second link joined to the first link among the plurality of links is a specific positional relationship.

4. The protective cover according to claim 1, wherein the first cover section is configured to hold a second link joined to a first link to which the imaging device is joined from among the plurality of links.

5. The protective cover according to claim 1, wherein the second cover section is configured to cover all of the imaging device.

6. The protective cover according to claim 1, wherein the second cover section is configured to cover a part of the imaging device.

7. The protective cover according to claim 1, wherein the imaging device covered by the second cover section is rotatable about an optical axis in the imaging device.

8. The protective cover according to claim 1, wherein the first cover section is provided with a cushioning member on a portion that contacts the arm when installed on the arm.

9. A medical observation apparatus comprising:
an arm including a plurality of links joined to each other by one or a plurality of joint sections;
an imaging device supported by and connected to the arm; and
a protective cover, wherein
the protective cover includes
a first cover section configured to hold at least a part of the arm, and
a second cover section configured to cover the imaging device, the second cover section being continuously connected to the first cover section,
an opening through which the arm passes is provided on the first cover section,
a protrusion configured to restrain a movement of a link of the plurality of the links joined to the held part of the arm is provided adjacent to the opening, the first cover section and the second cover section in combination form a cylindrical hollow space for accommodating the part of the arm and the imaging device, the first cover section and the second cover section extend in a longitudinal direction of the imaging device that is parallel to an optical axis of the imaging device, the opening is provided on a lateral side of the first cover section, and the protrusion is provided on the lateral side of the first cover section and adjacent to the opening.

10. The medical observation apparatus according to claim 9, wherein when the arm is in a predetermined storage state, a most spatially prominent part of the medical observation apparatus is not the imaging device covered by the protective cover.

11. The protective cover according to claim 1, wherein the first cover section and the second cover section in combination cover the part of the arm and the imaging device entirely, and no other opening is provided in the protective cover except for the opening.

12. The protective cover according to claim 1, wherein a second protrusion is provided on the lateral side of the first cover section and adjacent to the opening.

13. The protective cover according to claim 1, wherein the protrusion has a rectangular shape.

14. The protective cover according to claim 1, wherein
a second protrusion is provided on the lateral side of the first cover section and adjacent to the opening,
the protrusion and the second protrusion have a rectangular shape, and
the opening is provided between the protrusion and the second protrusion.

15. The protective cover according to claim 14, wherein the protrusion and the second protrusion extend in parallel from a plan view of the opening.

16. The protective cover according to claim 1, wherein the opening has a circular shape.

17. The protective cover according to claim 1, wherein the opening extends in parallel to the longitudinal direction of the imaging device that is parallel to the optical axis of the imaging device.

* * * * *